(12) United States Patent
Heikenfeld et al.

(10) Patent No.: US 12,262,990 B2
(45) Date of Patent: Apr. 1, 2025

(54) METHODS AND MATERIALS FOR PROLONGED SWEAT STIMULATION

(71) Applicant: University Of Cincinnati, Cincinnati, OH (US)

(72) Inventors: Jason C. Heikenfeld, Cincinnati, OH (US); Phillip Simmers, Powell, OH (US)

(73) Assignee: University of Cincinnati, Cincinnati, OH (US)

( * ) Notice: Subject to any disclaimer, the term of this patent is extended or adjusted under 35 U.S.C. 154(b) by 88 days.

(21) Appl. No.: 15/680,611

(22) Filed: Aug. 18, 2017

(65) Prior Publication Data

US 2018/0049681 A1 Feb. 22, 2018

Related U.S. Application Data

(60) Provisional application No. 62/377,087, filed on Aug. 19, 2016.

(51) Int. Cl.

| | | |
|---|---|---|
| A61B 5/145 | (2006.01) | |
| A61B 5/00 | (2006.01) | |
| A61B 5/053 | (2021.01) | |
| A61K 31/00 | (2006.01) | |

(Continued)

(52) U.S. Cl.
CPC .......... *A61B 5/14521* (2013.01); *A61B 5/053* (2013.01); *A61B 5/4266* (2013.01); *A61K 31/00* (2013.01); *A61N 1/0428* (2013.01); *A61N 1/325* (2013.01)

(58) Field of Classification Search
None
See application file for complete search history.

(56) References Cited

U.S. PATENT DOCUMENTS

| | | |
|---|---|---|
| 4,190,060 A | 2/1980 | Greenleaf et al. |
| 4,542,751 A | 9/1985 | Webster et al. |
| 4,756,314 A | 7/1988 | Eckenhoff et al. |

(Continued)

FOREIGN PATENT DOCUMENTS

| | | |
|---|---|---|
| CA | 2869469 A1 | 10/2013 |
| CN | 101489470 A | 7/2009 |

(Continued)

OTHER PUBLICATIONS

Spencer, H.J. "Programmable nanoampere constant current sources for iontophoresis". Med. & biol. Engng. (1971) 9: 693. https://doi.org/10.1007/BF02474650 (Year: 1971).*

(Continued)

*Primary Examiner* — May A Abouelela
*Assistant Examiner* — Samuel C Kim
(74) *Attorney, Agent, or Firm* — Wood Herron & Evans LLP

(57) ABSTRACT

A method for stimulating and sensing sweat includes dosing a sweat stimulant to skin effective to generate sweat at a generation rate of at least 0.1 nL/min/gland for a duration of six hours or more per dose of the sweat stimulant, and sensing generated sweat using a device placed on the skin comprising at least one sensor specific to an analyte in sweat. The dosing comprises at least one of: applying a charge density of less than 320 mC/cm$^2$/day or applying a one-time dose of the sweat stimulant.

27 Claims, 14 Drawing Sheets

(51) Int. Cl.
*A61N 1/04* (2006.01)
*A61N 1/32* (2006.01)

(56) References Cited

U.S. PATENT DOCUMENTS

| | | | |
|---|---|---|---|
| 4,820,263 A | 4/1989 | Spevak et al. | |
| 5,036,861 A | 8/1991 | Sembrowich et al. | |
| 5,050,604 A | 9/1991 | Reshef et al. | |
| 5,140,985 A | 8/1992 | Schroeder et al. | |
| 5,246,003 A | 9/1993 | DeLonzor | |
| 5,438,984 A | 8/1995 | Schoendorfer | |
| 5,480,651 A * | 1/1996 | Callaway | A61K 31/00 424/451 |
| 5,556,789 A | 9/1996 | Goerlach-Graw et al. | |
| 5,814,599 A | 9/1998 | Mitragotri et al. | |
| 5,944,662 A | 8/1999 | Schoendorfer | |
| 6,198,953 B1 | 3/2001 | Webster et al. | |
| 6,256,533 B1 | 7/2001 | Yuzhakov et al. | |
| 6,269,265 B1 | 7/2001 | Anderson | |
| 6,299,578 B1 | 10/2001 | Kurnik et al. | |
| 6,592,529 B2 | 7/2003 | Marett | |
| 6,666,821 B2 | 12/2003 | Keimel | |
| 7,190,986 B1 | 3/2007 | Hannula et al. | |
| 7,219,534 B2 | 5/2007 | Campbell | |
| 7,378,054 B2 | 5/2008 | Karmali | |
| 7,383,072 B2 | 6/2008 | Edmonson et al. | |
| 7,384,396 B2 | 6/2008 | Samuels et al. | |
| 7,749,445 B2 | 7/2010 | Masters | |
| 7,813,780 B2 | 10/2010 | Shah et al. | |
| 7,842,234 B2 | 11/2010 | Lauks et al. | |
| 7,959,791 B2 | 6/2011 | Kjaer et al. | |
| 8,125,539 B2 | 2/2012 | Takashima | |
| 8,128,889 B2 | 3/2012 | Fujimoto et al. | |
| 8,252,248 B2 | 8/2012 | Kramer | |
| 8,391,946 B2 | 3/2013 | Sugenoya et al. | |
| 8,565,850 B2 | 10/2013 | Martinsen et al. | |
| 8,593,287 B2 | 11/2013 | Hayter et al. | |
| 8,617,067 B2 | 12/2013 | Jain et al. | |
| 9,133,024 B2 | 9/2015 | Phan et al. | |
| 2002/0091312 A1 | 7/2002 | Berner et al. | |
| 2003/0135100 A1 | 7/2003 | Kim et al. | |
| 2003/0191376 A1 | 10/2003 | Samuels et al. | |
| 2003/0201194 A1 | 10/2003 | Heller et al. | |
| 2004/0082901 A1 * | 4/2004 | Phipps | A61N 1/0448 604/20 |
| 2004/0249310 A1 | 12/2004 | Shartle et al. | |
| 2004/0267189 A1 | 12/2004 | Mavor et al. | |
| 2005/0069925 A1 | 3/2005 | Ford et al. | |
| 2005/0106713 A1 | 5/2005 | Phan et al. | |
| 2005/0177035 A1 | 8/2005 | Botvinick et al. | |
| 2005/0192528 A1 | 9/2005 | Tapper | |
| 2005/0197554 A1 | 9/2005 | Polcha | |
| 2006/0004271 A1 | 1/2006 | Peyser et al. | |
| 2006/0062852 A1 | 3/2006 | Holmes | |
| 2006/0127964 A1 | 6/2006 | Ford et al. | |
| 2006/0253011 A1 | 11/2006 | Edmonson et al. | |
| 2006/0254341 A1 | 11/2006 | Campbell | |
| 2007/0027383 A1 | 2/2007 | Peyser et al. | |
| 2007/0032731 A1 | 2/2007 | Lovejoy et al. | |
| 2007/0179371 A1 | 8/2007 | Peyser et al. | |
| 2008/0015494 A1 | 1/2008 | Santini et al. | |
| 2008/0045816 A1 | 2/2008 | Jang et al. | |
| 2008/0114284 A1 * | 5/2008 | Anderson | A61N 1/0448 604/20 |
| 2008/0154179 A1 | 6/2008 | Cantor et al. | |
| 2008/0286349 A1 | 11/2008 | Nomoto et al. | |
| 2008/0306362 A1 | 12/2008 | Davis | |
| 2009/0076345 A1 | 3/2009 | Manicka et al. | |
| 2009/0204008 A1 | 8/2009 | Beilin | |
| 2009/0270704 A1 | 10/2009 | Peyser et al. | |
| 2010/0044224 A1 | 2/2010 | Kataky | |
| 2010/0063372 A1 | 3/2010 | Potts et al. | |
| 2010/0130843 A1 | 5/2010 | Caceres Galvez et al. | |
| 2010/0132485 A1 | 6/2010 | Erez et al. | |
| 2010/0179403 A1 | 7/2010 | Martinsen et al. | |
| 2010/0198521 A1 | 8/2010 | Haick | |
| 2011/0079521 A1 | 4/2011 | Revol-Cavalier | |
| 2011/0118656 A1 | 5/2011 | Eckhoff et al. | |
| 2011/0178380 A1 | 7/2011 | Chowdhury | |
| 2011/0196283 A1 | 8/2011 | Imran et al. | |
| 2011/0208458 A1 | 8/2011 | Pinter et al. | |
| 2011/0263613 A1 * | 10/2011 | Hendrickson | A61P 25/24 514/256 |
| 2011/0275918 A1 | 11/2011 | Yamashita et al. | |
| 2012/0004570 A1 | 1/2012 | Shimizu et al. | |
| 2012/0028283 A1 | 2/2012 | Hoss et al. | |
| 2012/0123220 A1 | 5/2012 | Iyer et al. | |
| 2012/0165626 A1 | 6/2012 | Irina et al. | |
| 2012/0209226 A1 | 8/2012 | Simmons et al. | |
| 2012/0229661 A1 | 9/2012 | Sekiguchi et al. | |
| 2012/0277697 A1 | 11/2012 | Haghgooie et al. | |
| 2012/0285829 A1 | 11/2012 | Mount et al. | |
| 2012/0317430 A1 | 12/2012 | Rahman et al. | |
| 2012/0323097 A9 | 12/2012 | Chowdhury | |
| 2013/0006079 A1 | 1/2013 | Feldman et al. | |
| 2013/0010108 A1 | 1/2013 | Hashizume et al. | |
| 2013/0013028 A1 | 1/2013 | Kriksunov et al. | |
| 2013/0053668 A1 | 2/2013 | Lin | |
| 2013/0053817 A1 * | 2/2013 | Yun | A61M 5/00 604/500 |
| 2013/0079605 A1 | 3/2013 | Bandaru et al. | |
| 2013/0099937 A1 | 4/2013 | Azimi | |
| 2013/0108667 A1 | 5/2013 | Soikum et al. | |
| 2013/0123595 A1 | 5/2013 | Currie et al. | |
| 2013/0183399 A1 | 7/2013 | Blow et al. | |
| 2013/0245388 A1 | 9/2013 | Rafferty et al. | |
| 2013/0306491 A1 | 11/2013 | Briman et al. | |
| 2013/0317333 A1 | 11/2013 | Yang et al. | |
| 2014/0012114 A1 | 1/2014 | Zevenbergen et al. | |
| 2014/0025000 A1 | 1/2014 | Currie et al. | |
| 2014/0206977 A1 | 7/2014 | Bahney et al. | |
| 2014/0275862 A1 | 9/2014 | Kennedy | |
| 2014/0276220 A1 | 9/2014 | Briscoe et al. | |
| 2014/0343371 A1 | 11/2014 | Sowers, II et al. | |
| 2015/0057515 A1 | 2/2015 | Hagen et al. | |
| 2015/0112164 A1 * | 4/2015 | Heikenfeld | A61B 5/0537 600/307 |
| 2015/0112165 A1 | 4/2015 | Heikenfeld | |
| 2016/0058354 A1 | 3/2016 | Phan et al. | |
| 2016/0066828 A1 | 3/2016 | Phan et al. | |
| 2016/0157768 A1 | 6/2016 | Braig et al. | |
| 2017/0325724 A1 * | 11/2017 | Wang | A61B 5/14521 |

FOREIGN PATENT DOCUMENTS

| | | |
|---|---|---|
| EP | 0282349 A2 | 9/1988 |
| EP | 0453283 A1 | 10/1991 |
| EP | 0634215 A1 | 1/1995 |
| EP | 1500937 A1 | 1/2005 |
| EP | 1637889 A1 | 3/2006 |
| EP | 2551784 A1 | 1/2013 |
| JP | H107-77525 A | 3/1995 |
| JP | H08-504513 A | 5/1996 |
| JP | 2007503958 A | 3/2007 |
| JP | 2007322260 A | 11/2007 |
| JP | 2008505330 A | 2/2008 |
| JP | 200963597 A | 3/2009 |
| JP | 2009118420 A | 5/2009 |
| WO | 9011519 A1 | 10/1990 |
| WO | 9414062 A1 | 6/1994 |
| WO | 0014535 A1 | 3/2000 |
| WO | 01/88525 A1 | 11/2001 |
| WO | 2006133101 A2 | 12/2006 |
| WO | 2007097754 A1 | 8/2007 |
| WO | 2007146047 A1 | 12/2007 |
| WO | 2008083687 A1 | 7/2008 |
| WO | 2008095940 A1 | 8/2008 |
| WO | 2009004001 A1 | 1/2009 |
| WO | 2009052321 A2 | 4/2009 |
| WO | 2010/017578 A1 | 2/2010 |
| WO | 2011117952 A1 | 9/2011 |
| WO | 2013152087 A2 | 10/2013 |
| WO | 2013181436 A1 | 12/2013 |
| WO | 2014001577 A1 | 1/2014 |

(56) References Cited

FOREIGN PATENT DOCUMENTS

| WO | 2014025430 A2 | 2/2014 |
|---|---|---|
| WO | 2015184072 A1 | 12/2015 |
| WO | 2015184097 A2 | 12/2015 |
| WO | 2016049019 A1 | 3/2016 |
| WO | 2016061362 A2 | 4/2016 |
| WO | 2016090189 A1 | 6/2016 |
| WO | 2016130905 A1 | 8/2016 |
| WO | 2016138087 A1 | 9/2016 |
| WO | 2017019602 A1 | 2/2017 |
| WO | 2017070640 A1 | 4/2017 |

OTHER PUBLICATIONS

Khurana, R.K. "Cholinergic dysfunction in Shy—Drager syndrome: Effect of the parasympathomimetic agent, bethanechol". Clinical Autonomic Research (1994) 4: 5. https://doi.org/10.1007/BF01828832 (Year: 1994).*
Shibasaki M, Crandall CG. "Effect of local acetylcholinesterase inhibition on sweat rate in humans". J Appl Physiol. (2001) 90(3): 757-762 (Year: 2001).*
Lang, E., Spitzer, A., Claus, D., Neundorfer, B. and Handwerker, H. O. Abstract of "Stimulation of sudomotor axon reflex mechanism by carbachol in healthy subjects and patients suffering from diabetic polyneuropathy". Acta Neurologica Scandinavica, (1995) 91: 251-254. (Year: 1995).*
Dhote, V., Bhatnagar, P., Mishra, P. K., Mahajan, S. C., & Mishra, D. K. (2012). Iontophoresis: a potential emergence of a transdermal drug delivery system;Scientia pharmaceutica, 80(1), 1-28. doi:10.3797/scipharm.1108-20 (Year: 2012).*
Braune, C., Erbguth, F., Birklein, F. (2001). Dose thresholds and duration of the local anhidrotic effect of botulinum toxin injections: Measured by Sudometry. British Journal of Dermatology, 144(1), 111-117. doi.org/10.1046/j.1365-2133.2001.03961.x (Year: 2001).*
Australian Patent Office, Notice of Acceptance for Patent Applicatin issued in Australian Application No. 2013243541 on Mar. 23, 2017 (3 pages).
Australian Patent Office, Patent Examination Report No. 1 issued in Australian Application No. 2013243541 on Nov. 25, 2016, 4 pages.
Chinese Patent Office, First Office Action issued in Chinese Application No. 201380028053.8 issued Dec. 21, 2105, 4 pages.
Chinese Patent Office, Second Office Action issued in Chinese Application No. 201380028053.8 issued Sep. 20, 2016, 8 pages (including English language translation).
Chinese Patent Office, Third Office Action issued in Chinese Application No. 201380028053.8 issued Mar. 20, 2017, 17 pages (including English language translation).
European Patent Office, Partial European Search Report issued in European Application No. 16203346.8-1657 on Mar. 24, 2017, 7 pages.
European Patent Office, Supplemental European Search Report issued in European Application No. 15799514.3-1657 on Dec. 7, 2017, 8 pages.
European Patent Office, Written Opinion of the International Search Authority / International Preliminary Report on Patentability for PCT/US2013/035092 mailed Oct. 16, 2014 (14 pages).
European Patent Office, Supplemental European Search Report issued in European Application No. 15799317.1-1657 on Dec. 21, 2017, 9 pages.
European Patent Office, Partial European Search Report issued in European Application No. 15800043.0-115 on Jan. 8, 2018, 13 pages.
Fu et al., "Controlled Reagent Transport in Disposable 2D Paper Networks", The Royal Society of Chemistry 2010, Lab Chip, 2010, 10, 918-920.
International Searching Authority, Search Report and Written Opinion issued in International Application No. PCT/US2014/061098 issued Dec. 12, 2014, 13 pages.
International Searching Authority, Invitation to Pay Additional Search Fees and, Where Applicable, Protest Fee, and Communication Relating to the Results of the Partial International Search, issued in International Application No. PCT/US2014/061083 dated Dec. 15, 2014, 6 pages.
International Searching Authority, Search Report and Written Opinion issued in International Application No. PCT/US2014/061083 mailed Mar. 31, 2015, 18 pages.
International Searching Authority, Search Report and Written Opinion issued in International Application No. PCT/US2015/032830 mailed Aug. 14, 2015, 9 pages.
International Searching Authority, Search Report and Written Opinion issued in International Application No. PCT/US2015/032843 mailed Oct. 26, 2015, 11 pages.
International Searching Authority, Search Report and Written Opinion issued in International Application No. PCT/US2015/032866 issued Nov. 19, 2015, 12 pages.
International Searching Authority, Search Report and Written Opinion issued in International Application No. PCT/US2015/032893 issued Nov. 13, 2015, 14 pages.
International Searching Authority, Search Report and Written Opinion issued in International Application No. PCT/US2015/040113 issued Feb. 4, 2016, 13 pages.
International Searching Authority, Search Report and Written Opinion issued in International Application No. PCT/US2015/051439 issued Dec. 28, 2015, 7 pages.
International Searching Authority, Invitation to Pay Additional Search Fees and, Where Applicable, Protest Fee, and Communication Relating to the Results of the Partial International Search, issued in International Application No. PCT/US2015/032843 mailed Aug. 18, 2015, 2 pages.
International Searching Authority, Invitation to Pay Additional Search Fees and, Where Applicable, Protest Fee, and Communication Relating to the Results of the Partial International Search, issued in International Application No. PCT/US2015/040113 mailed Dec. 1, 2015, 2 pages.
International Searching Authority, Invitation to Pay Additional Search Fees and, Where Applicable, Protest Fee, and Communication Relating to the Results of the Partial International Search, issued in International Application No. PCT/US2015/032866 mailed Aug. 31, 2015, 2 pages.
International Searching Authority, Invitation to Pay Additional Search Fees and, Where Applicable, Protest Fee, and Communication Relating to the Results of the Partial International Search, issued in International Application No. PCT/US2015/032893 mailed Aug. 31, 2015, 2 pages.
International Searching Authority, Search Report and Written Opinion issued in International Application No. PCT/US16/18635 mailed May 6, 2016, 12 pages.
International Searching Authority, Search Report and Written Opinion issued in International Application No. PCT/US16/17726 mailed May 12, 2016, 9 pages.
International Bureau, Notification Concerning Transmittal of International Preliminary Report on Patentability issued in International Application No. PCT/US13/35092 mailed Oct. 16, 2014, 14 pages.
International Searching Authority, Invitation to Pay Additional Fees and, Where Applicable, Protest Fee, and Communication Relating to the Results of the Partial International Search, issued in International Application No. PCT/US13/35092 mailed Aug. 26, 2013, 9 pages.
International Searching Authority, Search Report and Written Opinion issued in International Application No. PCT/US16/59392 mailed Oct. 28, 2016, 13 pages.
International Searching Authority, Search Report and Written Opinion issued in International Application No. PCT/US16/50928 mailed Sep. 9, 2016, 8 pages.
International Searching Authority, Search Report and Written Opinion issued in International Application No. PCT/US16/43862 mailed Oct. 19, 2016, 14 pages.
International Searching Authority, Search Report and Written Opinion issued in International Application No. PCT/US2017/013453 mailed May 18, 2017, 14 pages.
International Searching Authority, Search Report and Written Opinion issued in International Application No. PCT/US2017/039421 mailed Sep. 6, 2017, 10 pages.

(56) References Cited

OTHER PUBLICATIONS

International Searching Authority, Search Report and Written Opinion issued in International Application No. PCT/US2017/040588 mailed Sep. 25, 2017, 11 pages.

International Searching Authority, Search Report and Written Opinion issued in International Application No. PCT/US2017/047574 issued Nov. 16, 2017, 14 pages.

International Searching Authority, Search Report and Written Opinion issued in International Application No. PCT/US2017/052651 issued Dec. 12, 2017, 14 pages.

Japanese Patent Office, Office Action issued in Japanese Application No. 2015-504702 issued Jan. 20, 2017, 7 pages (including English language translation).

Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.

Sonner, Z., et al., "The microfluidics of the eccrine sweat gland, including biomarker partitioning, transport, and piosensing implications,"Biomicrofluidics, vol. 9, pp. 031301-1-031301-19, CrossMark, 19 pages.

Stoppa, Matteo, et al., "Wearable Electronics and Smart Tectiles: A Critical Review," Sensors, 2014, pp. 11957-11992, vol. 14 (36 pages).

European Patent Office, Official Communication for EP Application No. 13 718 933.8-1101 mailed Feb. 14, 2018 (5 pages).

European Patent Office, Extended European Search Report issued in European Application No. 15819306.0-1115 on Feb. 9, 2018 (9 pages).

International Searching Authority, Search Report and Written Opinion issued in International Application No. PCT/US2017/067495 mailed Mar. 1, 2018, 10 pages.

International Searching Authority/US, International Search Report and Written Opinion issued in corresponding PCT Application No. PCT/US2016/059392, mailed on Feb. 15, 2017 (12 pages).

European Patent Office, Extended Search Report issued in European Application No. 15844313.5 mailed on Mar. 15, 2018, 15 pages.

De Jong, J. et al., "Membranes and microfluidics: a review," Lab Chip, 2006, 6, 1125-1139 (15 pages).

Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.

European Patent Office, Extended Search Report issued for European Application No. 15800043.0-1115 mailed Apr. 16, 2018, 11 pages.

* cited by examiner

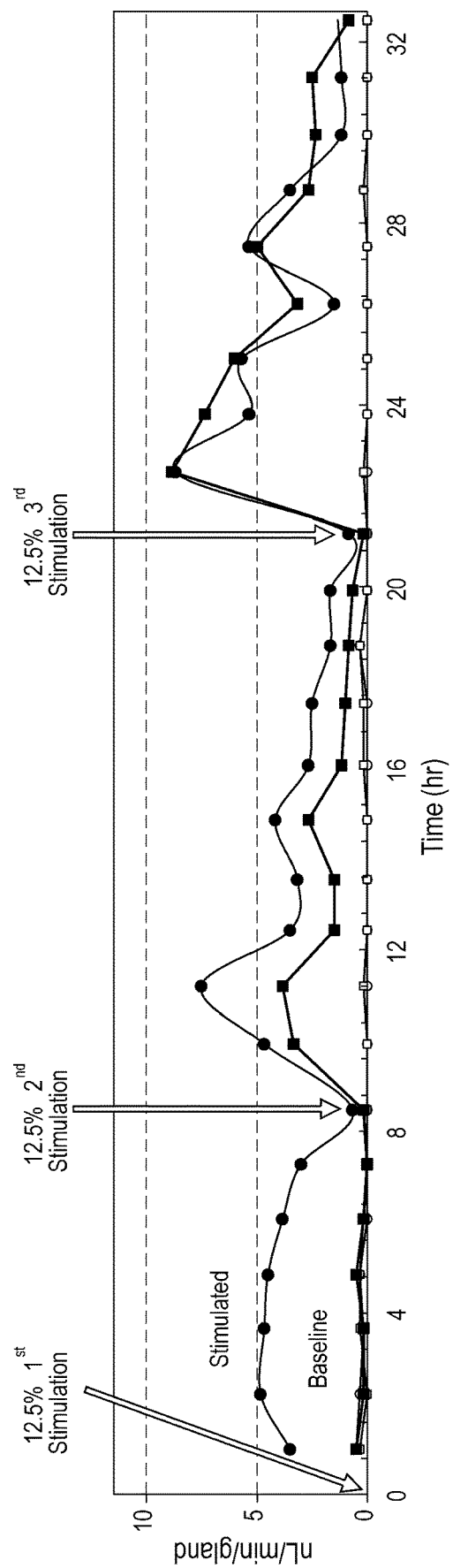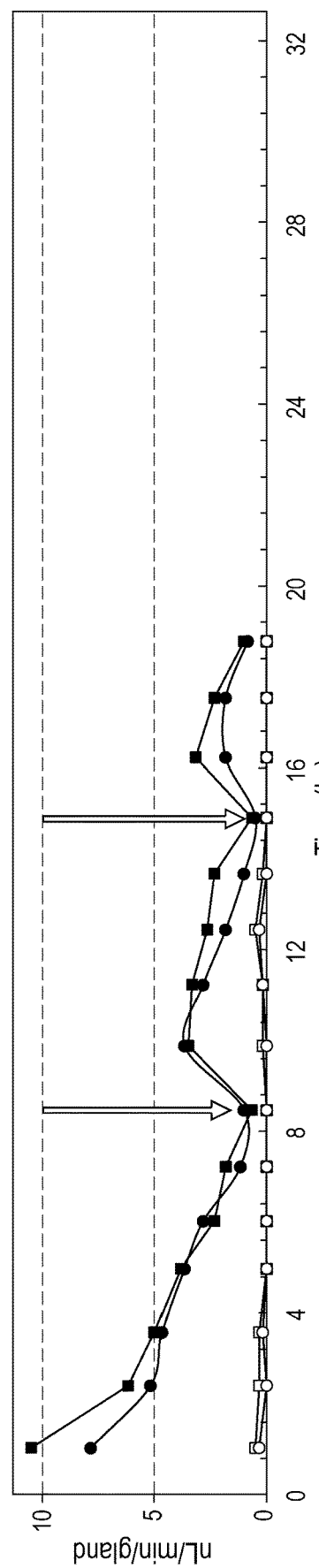
FIG. 7A
FIG. 7B

METHODS AND MATERIALS FOR PROLONGED SWEAT STIMULATION

BACKGROUND

Sweat sensing technologies have enormous potential for applications ranging from athletics, to neonatology, to pharmacological monitoring, to personal digital health, to name a few applications. Sweat contains many of the same biomarkers, chemicals, or solutes that are carried in blood and can provide significant information enabling one to diagnose ailments, health status, toxins, performance, and other physiological attributes even in advance of any physical sign. Furthermore, sweat itself, the action of sweating, and other parameters, attributes, solutes, or features on, near, or beneath the skin can be measured to further reveal physiological information.

Biosensing using sweat has many drawbacks and limitations. A need exists for improved methods of generating and sensing sweat.

SUMMARY OF THE INVENTION

Embodiments of the disclosed invention provide methods for sensing sweat on skin using a controlled sweat stimulant dosing regimen. In an embodiment, a method for sensing sweat on skin using a controlled sweat stimulant dosing regimen includes dosing a sweat stimulant to skin effective to generate sweat at a generation rate of at least 0.1 nL/min/gland for a duration of six hours or more per dose of the sweat stimulant, and sensing generated sweat using a device placed on the skin comprising at least one sensor specific to an analyte in sweat. The dosing comprises at least one of: applying a charge density of less than 320 mC/cm$^2$/day or applying a one-time dose of the sweat stimulant.

The objects and advantages of the disclosed invention will be further appreciated in light of the following detailed descriptions and drawings.

BRIEF DESCRIPTION OF THE DRAWINGS

FIGS. 7A-7C are graphs of the sweating responses based on repeated stimulations with 12.5% carbachol.

DETAILED DESCRIPTION OF THE INVENTION

One skilled in the art will recognize that the various embodiments may be practiced without one or more of the specific details described herein, or with other replacement and/or additional methods, materials, or components. In other instances, well-known structures, materials, or operations are not shown or described in detail herein to avoid obscuring aspects of various embodiments of the invention. Similarly, for purposes of explanation, specific numbers, materials, and configurations are set forth herein in order to provide a thorough understanding of the invention. Furthermore, it is understood that the various embodiments shown in the figures are illustrative representations and are not necessarily drawn to scale.

Reference throughout this specification to "one embodiment" or "an embodiment" means that a particular feature, structure, material, or characteristic described in connection with the embodiment is included in at least one embodiment of the invention, but does not denote that they are present in every embodiment. Thus, the appearances of the phrases "in an embodiment" or "in another embodiment" in various places throughout this specification are not necessarily referring to the same embodiment of the invention. Further, "a component" may be representative of one or more components and, thus, may be used herein to mean "at least one."

Figure 1:
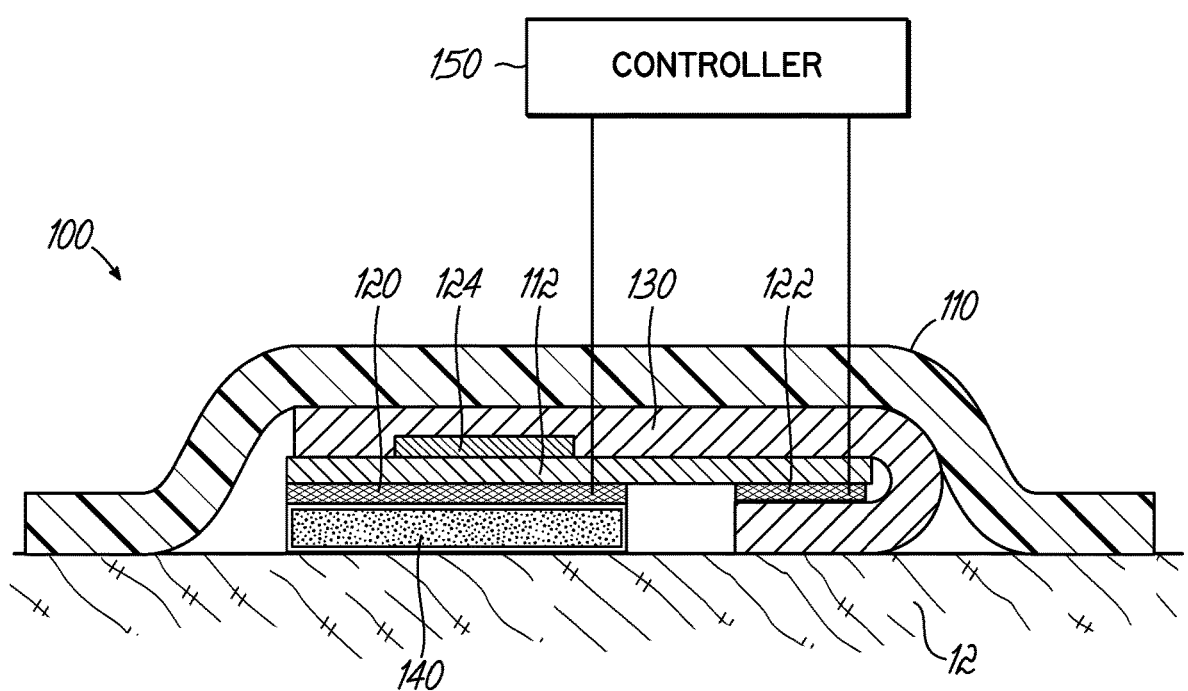
FIG. 1 is a cross-sectional view of a sweat sensing device according to an embodiment of the disclosed invention.
Figure 2A:
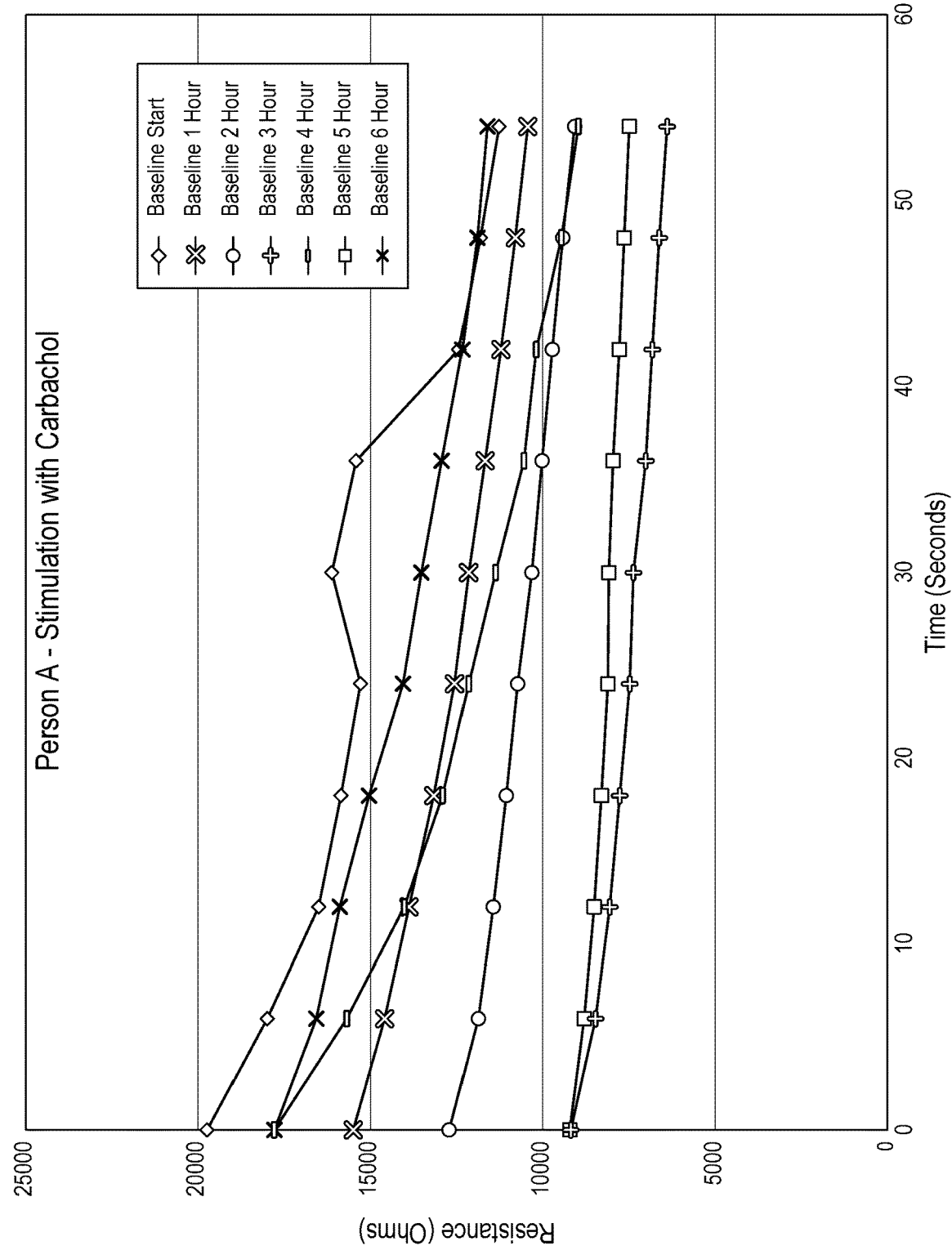
FIGS. 2A-2D are charts showing sweat stimulation with carbachol for Person A.
Figure 2B:
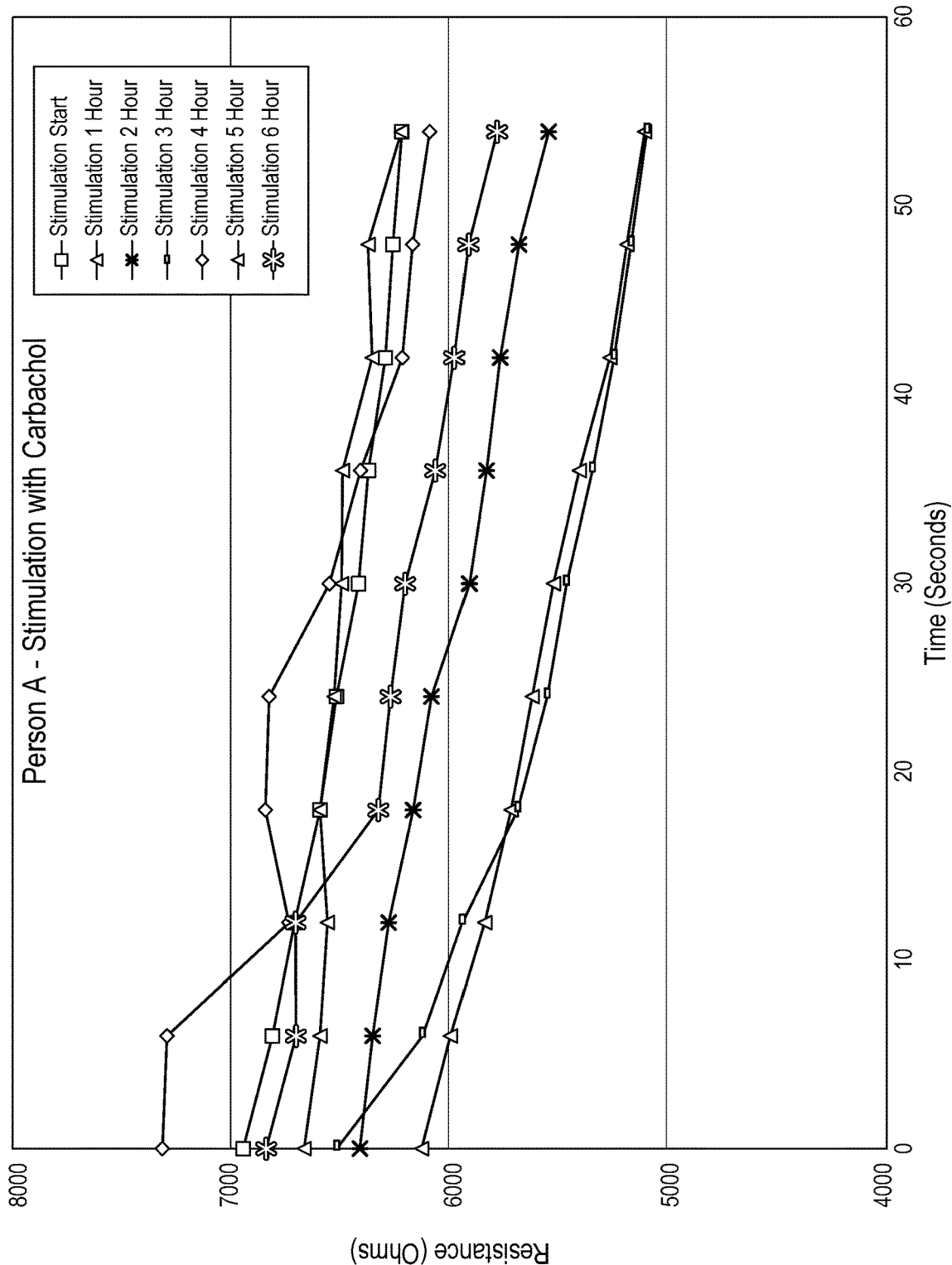
Figure 2C:
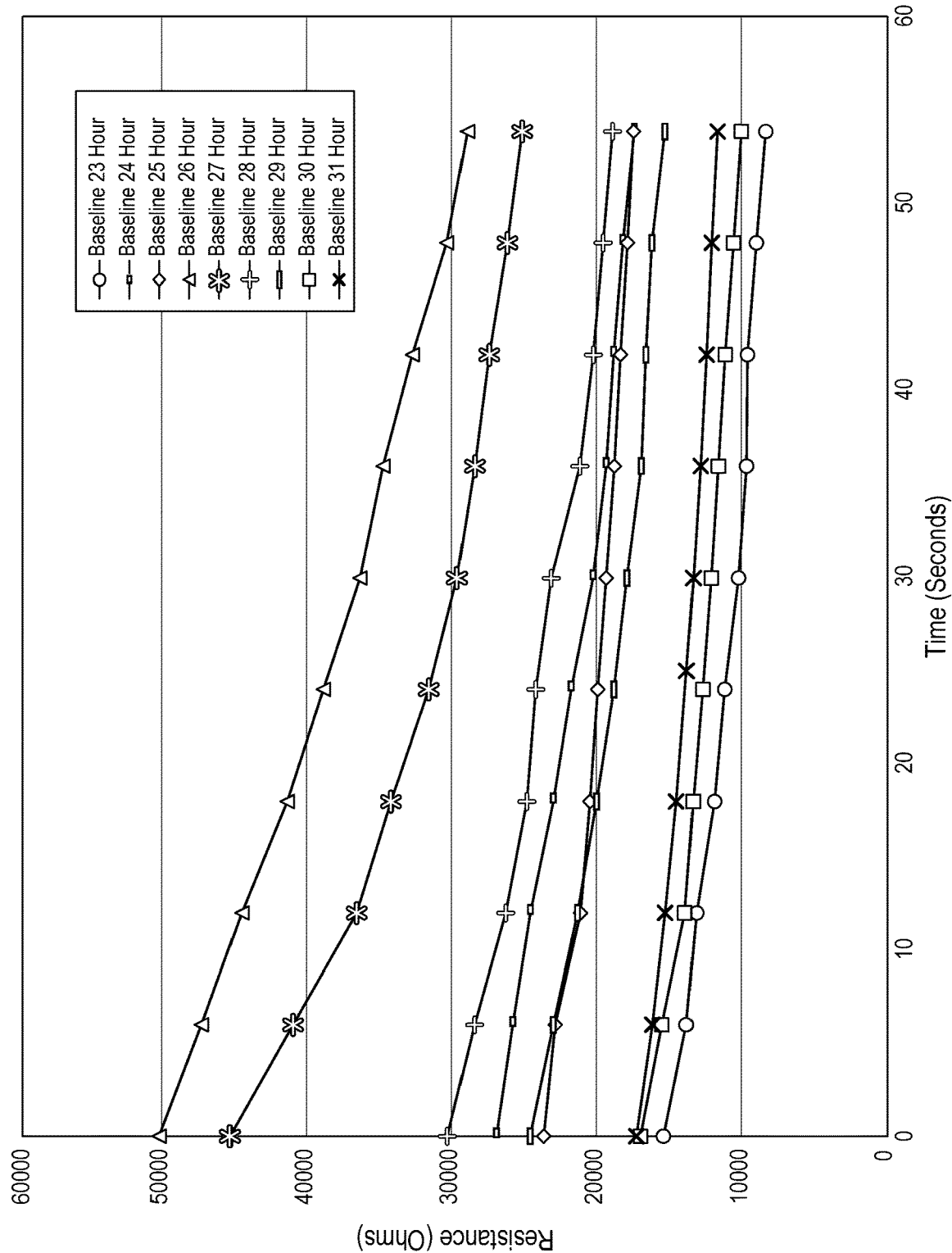
Figure 2D:
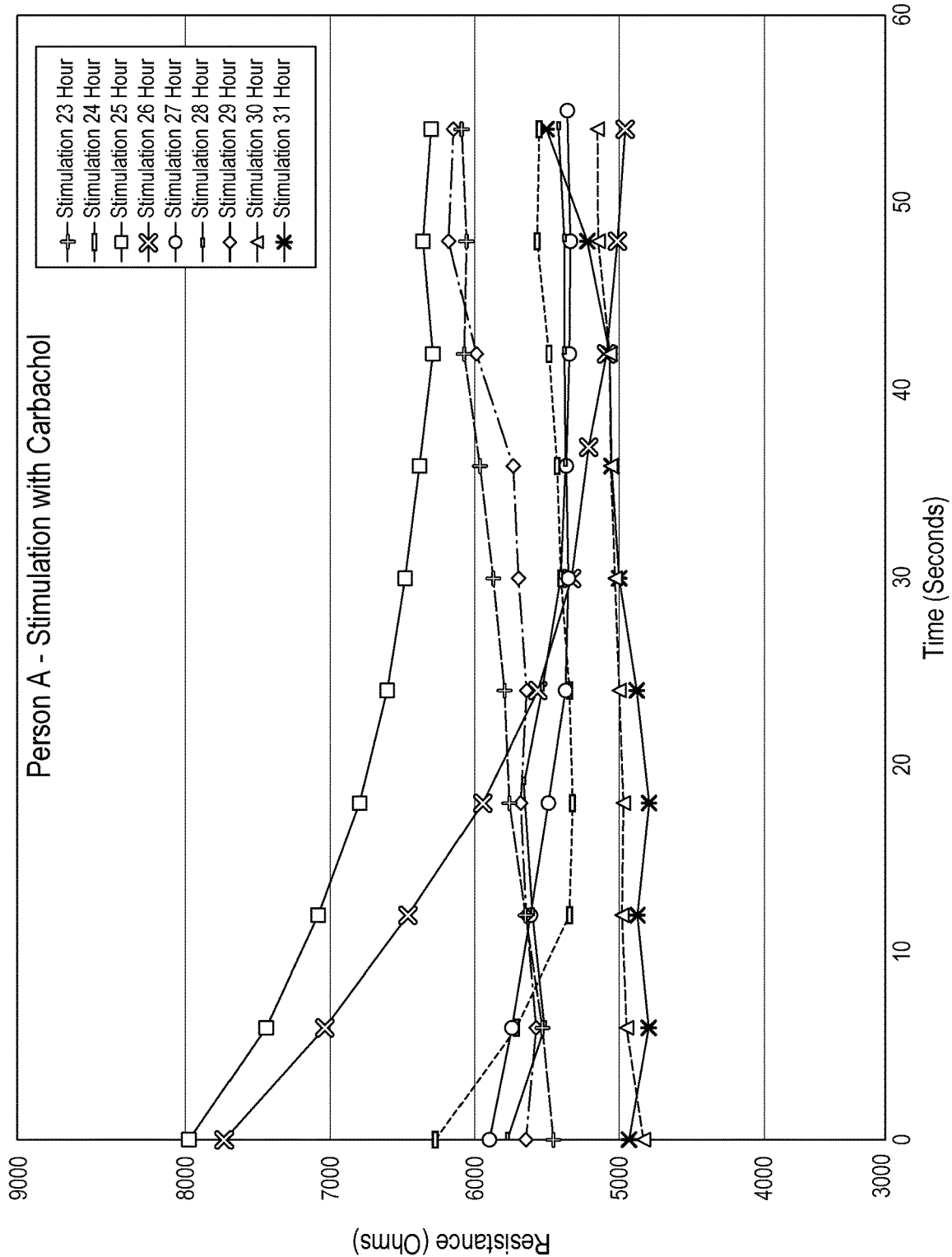
Figure 3A:
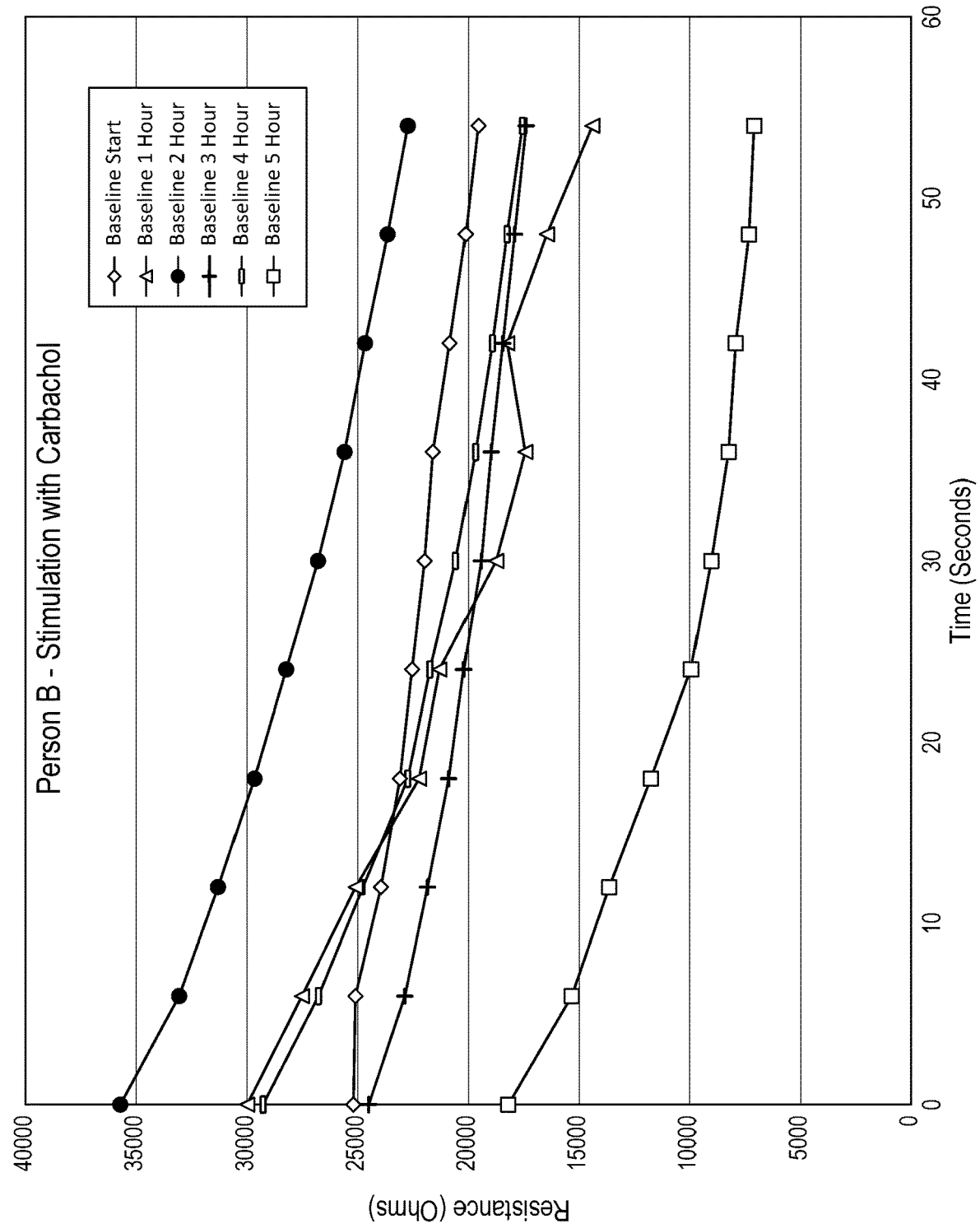
FIGS. 3A-3D are charts showing sweat stimulation with carbachol for Person B.
Figure 3B:
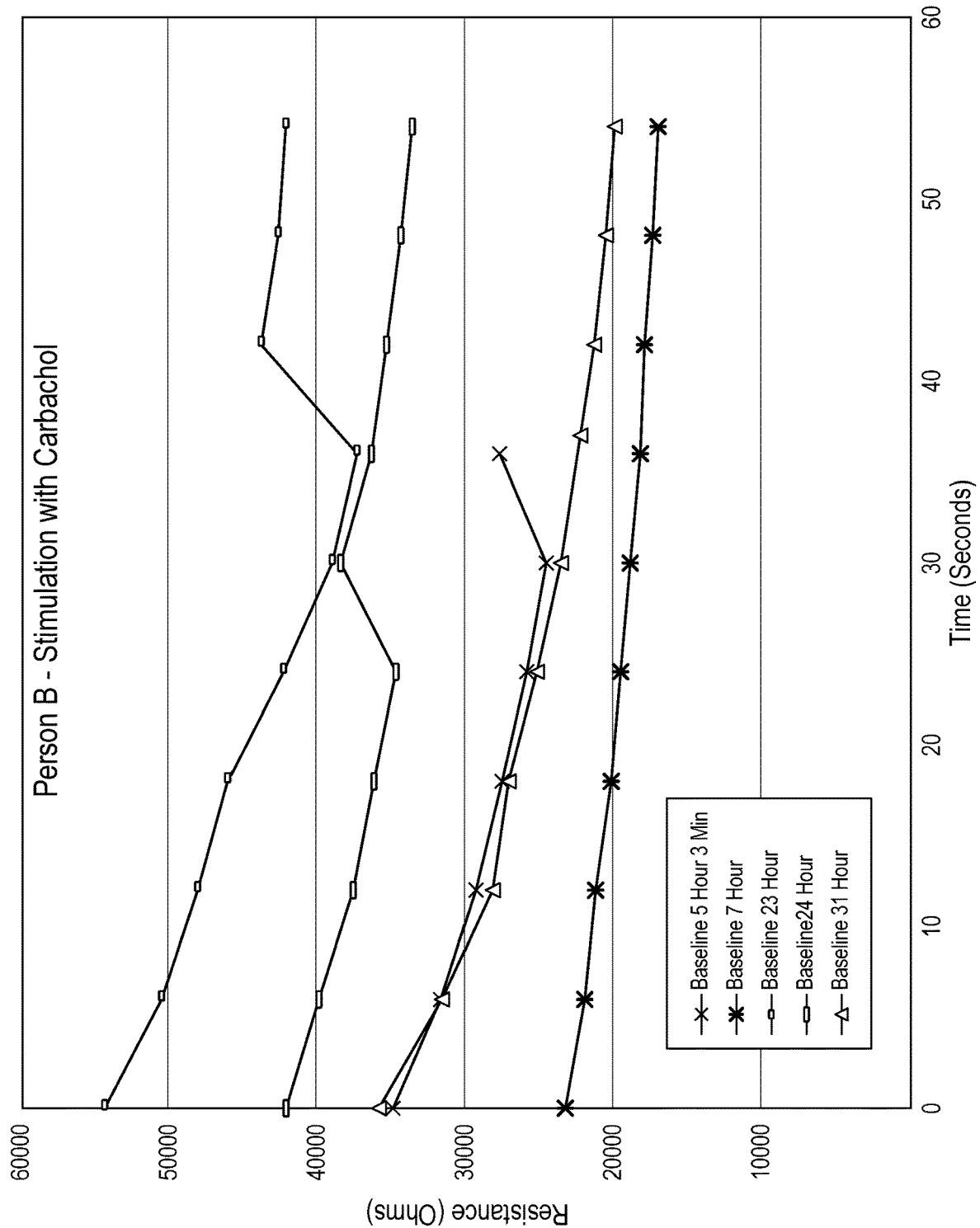
Figure 3C:
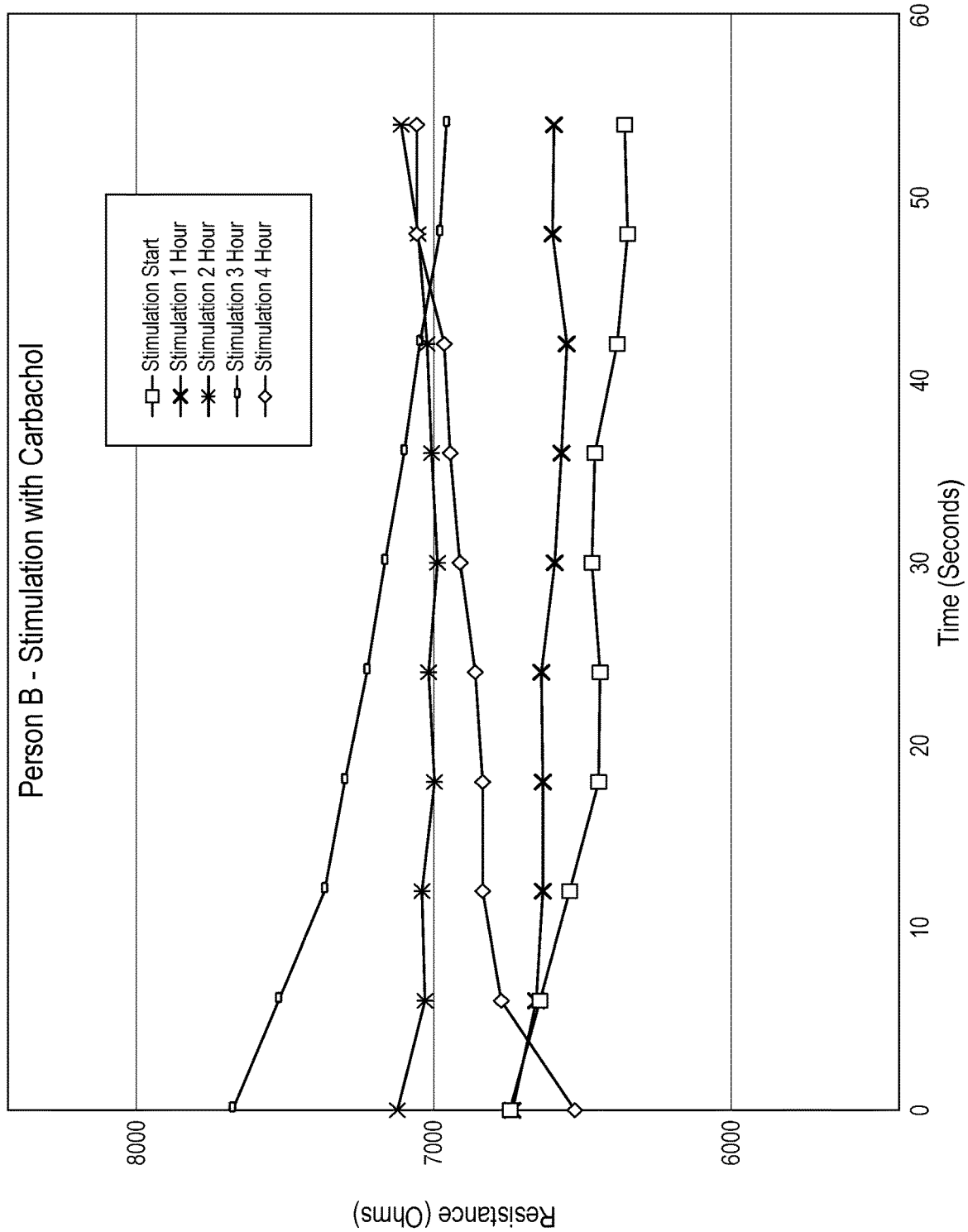
Figure 3D:
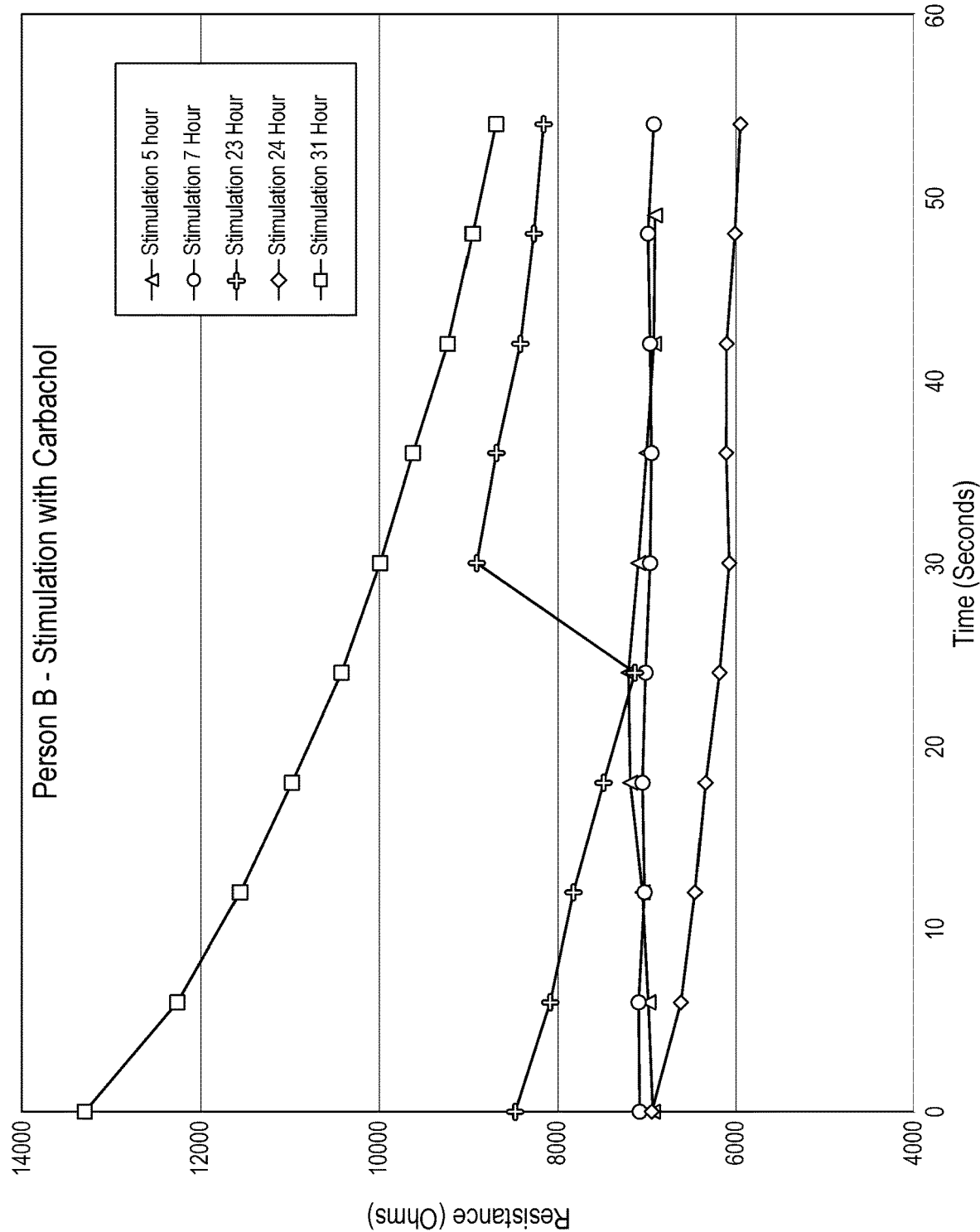

With reference to FIG. 1, a sweat sensing device 100 is placed on skin 12. The device 100 includes at least one sweat stimulant reservoir 140 containing a sweat stimulant. The sweat stimulant may be iontophoretically delivered or via another suitable transdermal delivery technique (e.g., diffusion, injection). The device 100 also includes an analyte-specific sensor 124 and a microfluidic component 130. The microfluidic component 130 collects sweat from the skin 12 and transports it to be sensed by the sensor 124. The device 100 further includes a breathable skin adhesive layer 110, a substrate 112, and electrodes 120, 122. Electrodes 120, 122 may be, for example, iontophoresis and/or electro-osmosis electrodes and/or counter-electrodes used to deliver the sweat stimulant to the skin 12. A controller 150 may control the electrodes 120, 122. The control of electrodes 120, 122 could be computationally controlled, controlled using simple analog electronic controls, or controlled through other suitable methods. All such control methods can be referred to as a control mechanism for controlling the dosage of one or more substances into the body. Dosage includes total amount of substance dosed into the body, the periodicity or rate, or other time or amount or other delivery factors which are important to delivery of a substance in a manner which is recommended or effective. The controller may limit the applied current or total dosage to ensure harmful or toxic dosages are never reached.

In an aspect of the disclosed invention, a sweat stimulation device, such as the device 100, may produce a prolonged response to sweat stimulation using a chemical agent that stimulates sweat and is slowly metabolized. A prolonged response to sweat stimulation may be, for example, 24 hours of sweat stimulation based on a single, one-time dose of the chemical agent. Exemplary sweat stimulation agents, such as acetylcholine, carbachol, and methacholine, may be delivered by iontophoresis to stimulate sweat. However, acetylcholine is rapidly metabolized by acetylcholinesterase (AChE), while other sweat stimulants, such as carbachol or methacholine, are metabolized much more slowly (see Table 1 below).

TABLE 1

Activity of Common Cholinomimetic Drugs

| Drug | Receptor Activity | | AChE Activity |
|---|---|---|---|
| | Muscarinic | Nicotinic | |
| Acetylcholine | +++ | +++ | +++ |
| Carbachol | ++ | +++ | − |
| Methacholine | +++ | + | ++ |
| Bethanechol | +++ | − | − |
| Muscarine | +++ | − | − |
| Pilocarpine | ++ | − | − |
| Oxotremorine | ++ | − | − |

Embodiments of the disclosed invention may include sweat collection from areas of skin in which the sweat generation was indirectly or directly stimulated. For example, the device 100 directly stimulates sweat beneath the device 100, which is collected by the microfluidic component 130. Suitable devices capable of indirectly stimulating sweat are described in International Patent Application No. PCT/US16/17726, the disclosure of which is incorporated herein in its entirety. As yet another example, a sweat sensing device could be applied after the stimulation has been directly applied, such as with a device described in International Patent Application No. PCT/US16/50928, the disclosure of which is incorporated herein in its entirety.

The total charge density applied per day may exceed that needed to achieve 24 hours of sweat stimulation. Embodiments of the disclosed invention may include total charge densities of equal to or less than: 320 $mC/cm^2$/day, 160 $mC/cm^2$/day, 80 $mC/cm^2$/day, 40 $mC/cm^2$/day, 20 $mC/cm^2$/day, 10 $mC/cm^2$/day, 5 $mC/cm^2$/day, 2 $mC/cm^2$/day, or 1 $mC/cm^2$/day. Each of these total charge densities could correspond to a single dose of the sweat stimulant delivered once per day to the total dosage of doses applied more than once per day (e.g., a single dose of 160 $mC/cm^2$ or three doses of 80 $mC/cm^2$ each to reach a total charge density of 160 $mC/cm^2$/day).

In an aspect of the disclosed invention, the charge density could also be normalized to the quantity of dose per day based on the desired total stimulated sweat amount. In an embodiment, the charge density may be determined such that the stimulated sweat amount achieved is, for example, greater than 1,400 nL/gland/(40 $mC/cm^2$). Thus, a charge density of 40 $mC/cm^2$ may provide a stimulated sweat amount of greater than 1,400 nL/gland/dose.

A charge density of 40 $mC/cm^2$ may provide a sweat rate of greater than 1 nL/min/gland for 24 hours (see Example 1). Pilocarpine, at a charge density of 40 $mC/cm^2$, can typically achieve an average sweat rate of about 1-4 nL/min/gland for 90 minutes, which is only a generated or stimulated sweat amount of 360 nL/min/gland/dose or less. In various embodiments of the disclosed invention, a stimulated sweat generation rate of greater than: 0.1 nL/min/gland, 0.2 nL/min/gland, 0.5 nL/min/gland, 1 nL/min/gland, 2 nL/min/gland, or 5 nL/min/gland can be achieved for a duration of six hours per dose or more. These sweat generation rates may also be achieved for longer durations, such as 24 hours or 30 hours.

For a 24-hour average of 1 nL/min/gland, embodiments of the disclosed invention may generate stimulated sweat at an amount greater than one of: 5,600 nL/gland/dose, 2,800 nL/gland/dose, 1,400 nL/gland/dose, 700 nL/gland/dose, or 350 nL/gland/dose where the dose is a single, one-time dosing of the sweat stimulant.

In embodiments of the disclosed invention, the total charge density could be applied in one dose or could be divided amongst multiple smaller sub-doses over 24 hours (e.g., 10 $mC/cm^2$ every 6 hours). In an aspect of the disclosed invention, the number of doses per day may vary based on the sweat stimulant used. For example, pilocarpine would last on average 90 minutes, which would require 16 repeated doses to provide continuous sweat generation and sampling throughout one day. Therefore, the disclosed invention may include a device capable of 24 hours of sweat stimulation using less than or equal to 10 stimulations (i.e., sub-doses), or less than or equal to 5 stimulations, or less than or equal to 2 stimulations, or only 1 stimulation. Therefore, the term total charge density described above (e.g., 40 $mC/cm^2$/day) could be achieved through multiple stimulation doses (i.e., sub-dosings) or a single, one-time stimulation dose.

Stimulation area can be as little as 0.5 $cm^2$, 0.2 $cm^2$, 0.1 $cm^2$, or 0.05 $cm^2$, which for even 0.05 $cm^2$ and 100 active glands/$cm^2$ would provide as many as 5 active glands for sweat sampling. For less than 40 $mC/cm^2$, this translates to a total applied charge of less than 20 mC/day, less than 8 mC/day, less than 4 mC/day, 2 mC/day and, for lower sweat generation rates, can even be less than 1 mC/day. Units of charge density ($mC/cm^2$) can be transferred into stimulant dose density ($mg/cm^2$) using conversion based on molecular weights, which for 75 mC total are listed in Table 3 for several examples.

TABLE 3

| Carbachol (mg) | Acetylcholine (mg) | Methacholine (mg) | Pilocarpine (mg) |
|---|---|---|---|
| 0.142 | 0.1136 | 0.125 | 0.162 |

Because some of the sweat stimulants described herein are very slowly metabolized, they can also be applied practically by injection or by passive diffusion. Therefore, unless the terms such as iontophoresis and/or mC are used, sweat stimulation or delivery of a sweat stimulant may include any suitable localized method, such as passive diffusion. For example, carbachol could be placed in propylene glycol or even just water and passively diffused through or into the skin to stimulate sweat.

An embodiment of the disclosed invention may also use a plurality of different sweat stimulants. For example, a hydrogel such as agar could contain both carbachol and methacholine, as some subjects may have a stronger or longer duration response to methacholine instead of carbachol. As a result, a single stimulation gel could be used which generally works across the variety of subjects found in the general population. Furthermore, new stimulants may be developed in the future. For example, carbachol has both strong nicotinic and muscarinic activity. A first stimulant could be developed that is fully optimized for a strong and prolonged muscarinic response, and a second stimulant could be developed that is fully optimized for a strong and prolonged nicotinic response. Therefore, a stimulant gel could contain both the first and second stimulants and deliver them into the skin by iontophoresis, and potentially exceed the performance of a single stimulant such as carbachol. Such a plurality of stimulants could also be delivered by other means, such as passive diffusion. In a mixture of stimulants, the mixture could comprise primarily one stimulant such that the primary stimulant makes up 50% or greater by weight of the total amount of stimulants.

An embodiment of the disclosed invention may also use one or more sweat stimulants along with local inhibitors of metabolism of the sweat stimulants, such as acetylcholinesterase inhibitors. Further, in an embodiment, the sweat stimulant may primarily include an acetylcholinesterase inhibitor. An acetylcholinesterase inhibitor passively causes sweat to be generated compared to the active nature of a stimulant such as carbachol. Acetylcholinesterase inhibitors include those that are reversible, irreversible, or quasi-irreversible (also called pseudo-irreversible) and include those such as carbamates and other chemicals.

Lastly, the above examples and parameters are provided for average subjects. It will be recognized that subjects with rare conditions or disorders may skew interpretation of the embodiments disclosed herein, but are practically irrelevant in context of a large number of users from the population.

In order to facilitate a more complete understanding of the embodiments of the invention, the following non-limiting examples are provided.

Example 1

Sweat was stimulated on two persons (A and B) using for each person a current of 0.5 mA and a charge of 75 mC applied over a total stimulated area of 1.9 $cm^2$ for a time of 150 seconds. Thus, the total charge density was 75 mC/1.9 $cm^2$ or about 40 $mC/cm^2$, and the estimated dose of carbachol delivered to the skin was 0.142 mg. The charge density and stimulant dose estimates may vary based on other ionic impurities that are also dosed (e.g., sodium dosed could decrease the amount of carbachol dosed). The effect of the dosed ionic impurities can be estimated or quantified in any given case by analytical chemistry techniques. The actual stimulant dose may be less than the estimated dose, which would make the results demonstrated here and in Example 2 even more impressive. The stimulated area was divided among two circular test sites that were approximately 1 inch apart. Skin impedance was measured using a Gamry Potentiostat using 2 kHz and 1 V peak to peak sinewave. The electrical resistance results are plotted in FIGS. 2A-2D and 3A-3D for Persons A and B, respectively (the data has been separated into four charts for each person for the sake of clarity). The baseline plots were measured at a control site (i.e., non-stimulated skin) positioned within 1 inch of the stimulation site. Both Persons A and B clearly showed at least 24 hours of sweat stimulation from a single dose. Person A showed at least 31 hours of sweat stimulation from a single dose. Several baseline data sets are lower in electrical resistance because of natural sweating events, but the stimulated areas do not increase in resistance, which clearly indicates a constant production of sweat due to chemical stimulation with carbachol.

Figure 4:
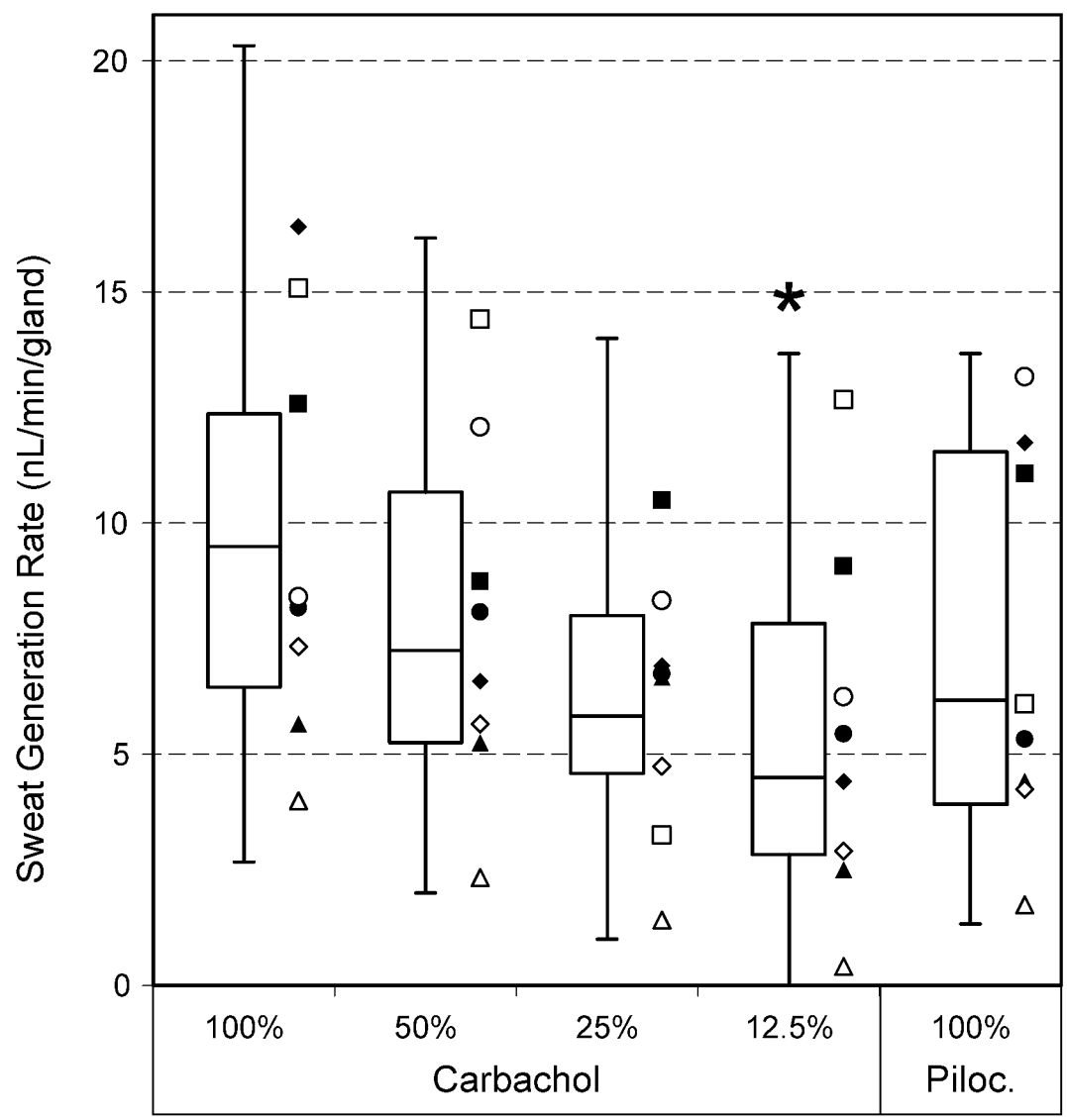
FIG. 4 is a graph including a bar and whisker graph of initial sweat generation rates at specific doses and a scatter plot for the average initial sweat rate subject is to the right of the bar and whisker graph in which * indicates a significant difference of means of that dose to 100% carbachol (p-value less than 0.05).

Sweat rates in nL/min/gland were also quantified using visual testing and gravimetric testing. Results from Person B are shown in FIG. 4 for a skin site of about 1 $cm^2$ of skin at 25 hours after stimulation. Approximately 130 active glands were counted per $cm^2$. Filter papers were weighed, placed on stimulated and control sites for 10 minutes under a plastic wrap to prevent evaporation, and immediately weighed again, and then sweat generation rates were calculated. The control sites exhibited no increase in weight with only the exception of one paper that suggested a sweat rate of 0.01 nL/min/gland. The data for the stimulated sites 1 and 2 (paper measurements taken from each of the two stimulation areas) is shown in Table 2.

TABLE 2

| Subject | Site | Time after Stimulation (hours) | Sweat Generation Rate (nl/min/gland) |
|---|---|---|---|
| A | 1 | 4 | 6.4 |
| A | 2 | 4 | 4.6 |
| B | 1 | 5 | 8.3 |
| B | 2 | 5 | 9.4 |
| A | 1 | 23 | 3.3 |
| A | 2 | 23 | 3.1 |
| B | 1 | 23 | 0.3 |
| B | 2 | 23 | 2.7 |

The above experiment in carbachol sweat stimulation can be interpreted in several ways. As described above, the total charge density was about 40 $mC/cm^2$ per day. The total charge density applied per day exceeded that needed to achieve 24 hours of sweat stimulation, and lower charge densities were observed to also produce sweat generation for 24 hours as well. Furthermore, some applications may benefit from sweat generation rates of only 0.1's nL/min/gland (10× lower than that illustrated in this example). As a result, the dosages required could be even lower.

The 40 $mC/cm^2$ charge density applied in Example 1 achieved a sweat rate of greater than 1 nL/min/gland for 24 hours. Further, a charge density of less than 40 $mC/cm^2$ achieved a stimulated sweat amount of greater than 1,400 nL/gland/dose. Pilocarpine, at a charge density of 40 $mC/cm^2$, can typically achieve an averaged sweat rate of only about 1-4 nL/min/gland for 90 minutes, which is only a generated or stimulated sweat amount of 360 nL/min/dose or less. In fact, average sweat rates observed were higher than 1 nL/min/gland (greater than 2 nL/min/gland average) for 24 hours for even half the dose.

Example 2

On 8 subjects, sweat was stimulated utilizing carbachol four times as detailed in Table 4 and one additional time utilizing pilocarpine. The stimulated area was divided among two circular test sites with areas of 0.88 $cm^2$ that were approximately 1 inch apart, which provides a total stimulation area of 1.76 $cm^2$. The carbachol doses in Table 4 are shown as percentages of the applied charge density compared to the charge density of pilocarpine applied by the commercial Wescor Nanoduct product, which is a charge density of 42 $mC/cm^2$. The pilocarpine was dosed over 150 seconds using a current of 0.28 $mA/cm^2$ and a charge density of 42 $mC/cm^2$, which delivered approximately 90.65 $\mu g/cm^2$.

TABLE 4

| Carbachol Dose | Current ($mA/cm^2$) | Time (s) | Charge ($mC/cm^2$) | Carbachol Delivered ($\mu g/cm^2$)* |
|---|---|---|---|---|
| 12.50% | 0.28 | 18.75 | 5.25 | less than 9.94 |
| 25% | 0.28 | 37.5 | 10.5 | less than 19.88 |
| 50% | 0.28 | 75 | 21 | less than 39.76 |
| 100% | 0.28 | 150 | 42 | less than 79.53 |

Figure 5:
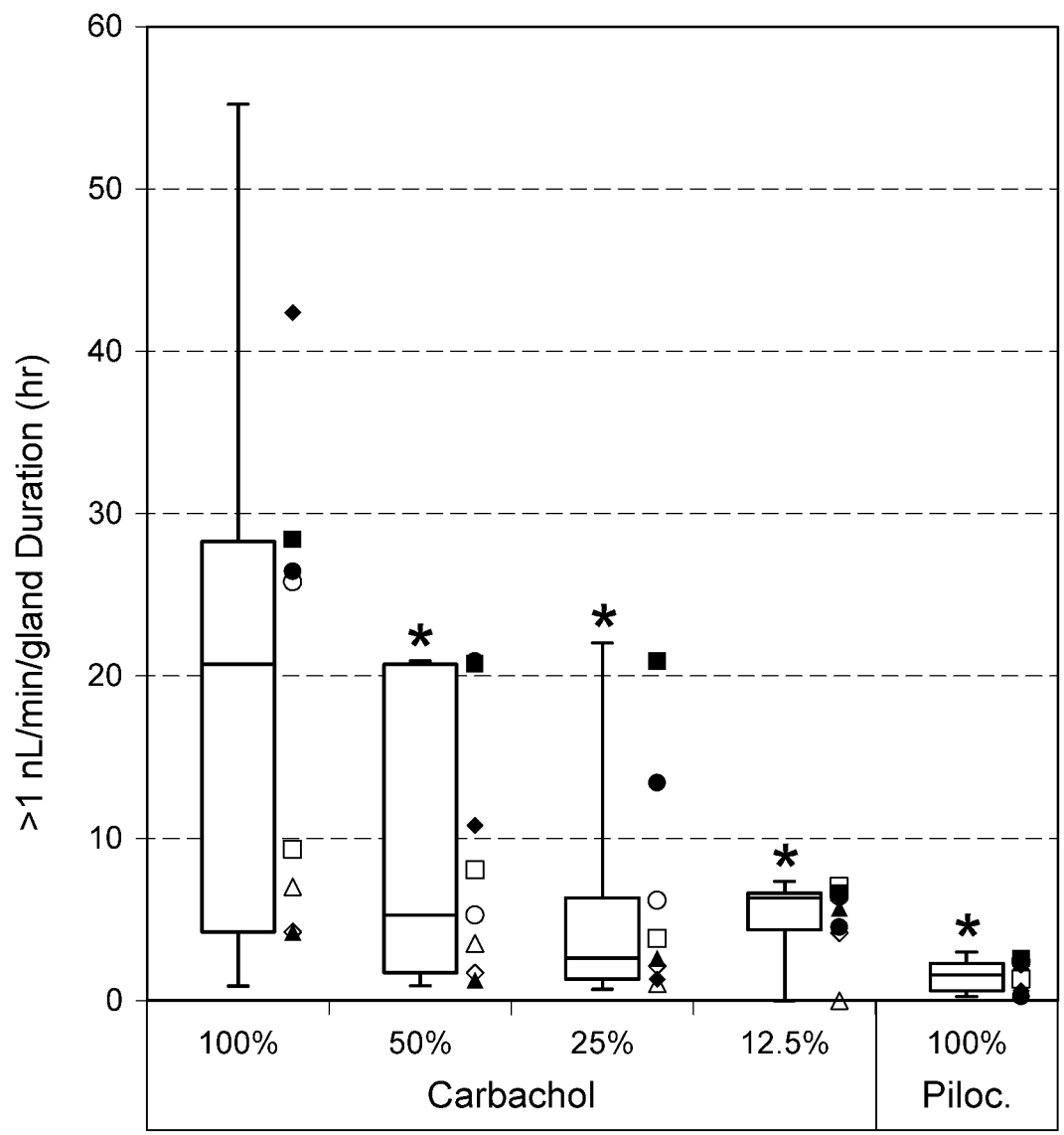
FIG. 5 is a graph including a bar and whisker graph of the duration of sweating responses with a 1 nL/min/gland cut off at specific doses and a scatter plot for the average duration between medial and later locations for each subject is to the right of the bar and whisker graph in which * indicates a significant difference of means of that dose to 100% carbachol and pilocarpine (p-value less than 0.05) and ** indicates a significant difference of means of that dose to 100% carbachol (p-value less than 0.05).
Figure 6:
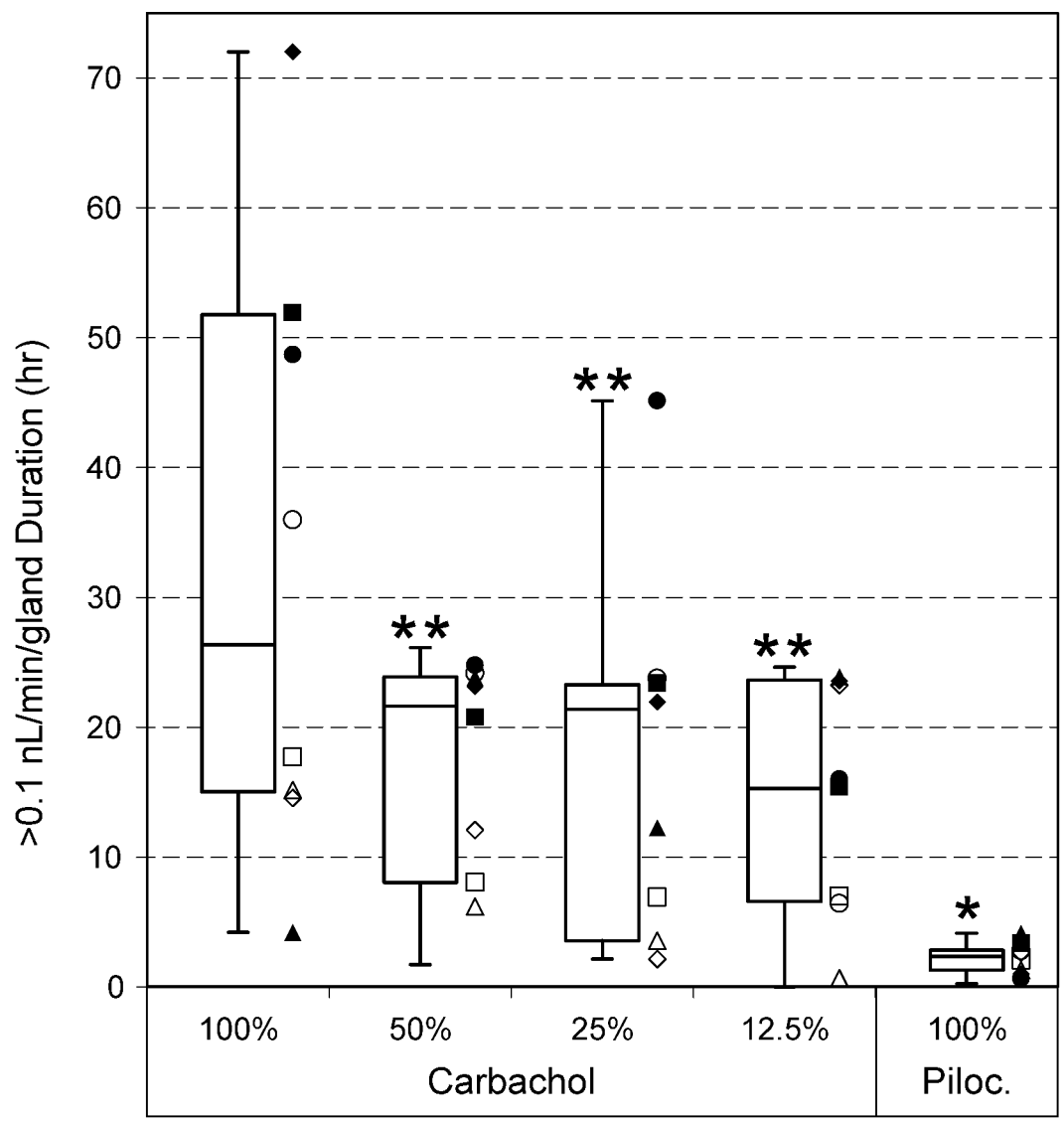
FIG. 6 is a graph including a bar and whisker graph of the duration of sweating responses with a 0.1 nL/min/gland cut off at specific doses and a scatter plot for the average duration between medial and later locations for each subject is to the right of the bar and whisker graph in which * indicates a significant difference of means of that dose to 100% carbachol (p-value less than 0.05).
Figure 7C:
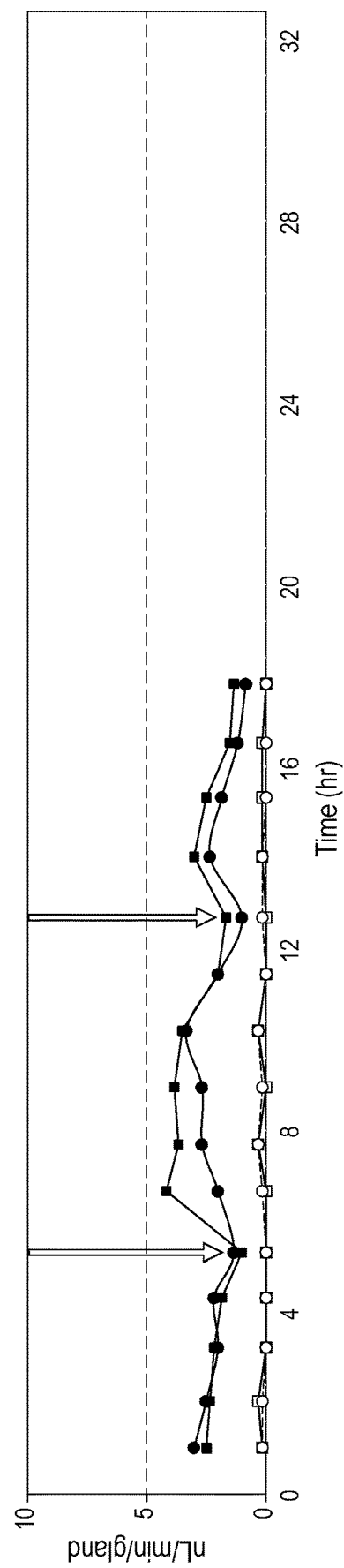

*Theoretical maximum amount, realistically less than 30% of the total delivered is actually delivered Sweat rate was determined by a gravimetric test. Filter papers were weighed, placed on stimulated and control sites for 10 minutes under a specially designed acrylic holder that prevented any wicking of sweat from neighboring areas and prevented evaporation. The papers were immediately weighed again, and then sweat generation rates were calculated. The results from the gravimetric testing are plotted in FIGS. 4-6. Additionally, three subjects received three consecutive doses of 12.5% carbachol once the sweat rate had fallen below 1 nL/min/gland. The results from the repeated stimulation testing of subjects 1-3 are plotted in FIGS. 7A-7C, respectively.

The results can be interpreted in several ways. From a fundamental perspective, the results provide insights into the long duration and inter-subject variability for sweating induced by a cholinergic agent that is weakly or not susceptible to metabolism by AChE. In particular, the results show sustained sweating following a single iontophoretic dose of carbachol that is much longer than commonly observed for pilocarpine.

From an applied perspective, the duration and magnitude of the sweating responses achieved here are important for enabling wearable sweat biosensing for individuals at rest. Carbachol now presents a potential option for applications where it is desired to measure analytes in sweat continuously for 24 hours or more.

The results indicate that greater volumes of sweat samples may be generated with less stress on the subject (e.g., no need for a prolonged thermal load). Second, larger molecular weight and hydrophilic analytes undergo dilution that depends on sweat generation rate. Therefore, the results delineate collection windows where the sweat generation rate can be fairly stable and therefore analyte dilution can be predicted.

Although half of the subjects exhibited greater than 24 hours of sweating at greater than 1 nL/min/gland with a single 100% dose, several subjects fell well short of this target. Four of the subjects exhibited sweating responses greater than 24 hours and three subjects exhibited sweating responses that lasted for greater than 48 hours. A sweating response of greater than 48 hours was surprising, but equally surprising was just how short the response was for some of the other subjects.

The triple repeated 12.5% dosage stimulation data represent a technological solution to achieving greater than 24 hour localized stimulation even for the subjects who had short stimulation responses. In particular, examining the raw data single dosage experiments, the 12.5% stimulation shows that 5 out of 8 subjects exhibit a stimulated sweating response of greater than 0.1 nL/min/gland for greater than 8 hours. The exceptions (subjects e, g, h) at least showed greater than 1 nL/min/gland for greater than 7 hours at 100% dosage. Therefore, all subjects in this study should achieve greater than 24 hour sweat stimulation if the stimulant is dosed 3 to 4 times or less at 100% per dose or less. Smaller stimulation and sweat sampling areas could be utilized to offset the increased dose of carbachol due to repeated dosing.

While specific embodiments have been described in considerable detail to illustrate the disclosed invention, the description is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A method comprising:
applying a plurality of doses of a sweat stimulant to skin effective to generate sweat at or above a minimum sweat generation rate for a duration, wherein the applying comprises applying a charge density that is equal to or less than 320 mC/cm$^2$/day, wherein the minimum sweat generation rate is greater than or equal to 0.1 nL/min/gland, wherein the sweat stimulant is selected from the group consisting of acetylcholine, carbachol, methacholine, bethanechol, muscarine, pilocarpine, oxotremorine, or a combination thereof, wherein the duration is greater than or equal to six hours, wherein applying the plurality of doses of a sweat stimulant comprises:
applying a first dose;
measuring a sweat generation rate to establish a measured sweat generation rate for the duration;
applying at least one subsequent dose in response to the measured sweat generation rate falling below a predetermined sweat rate during the duration, the predetermined sweat rate being greater than the minimum sweat generation rate;
collecting a sweat sample from the skin; and
receiving a measurement of a characteristic of an analyte in the sweat sample.

2. The method of claim 1, wherein the minimum sweat generation rate is greater than 0.2 nL/min/gland.

3. The method of claim 1, wherein an amount of sweat generated per gland is greater than 5,600 nL/gland/dose.

4. The method of claim 1, wherein the sweat stimulant comprises one of the following: carbachol, methacholine, bethanechol, pilocarpine, or muscarine.

5. The method of claim 1, wherein the applying the sweat stimulant further includes applying a local inhibitor of metabolism of the sweat stimulant.

6. The method of claim 5, wherein the local inhibitor is an acetylcholinesterase inhibitor.

7. The method of claim 1, wherein the sweat stimulant comprises a plurality of chemicals capable of stimulating sweat.

8. The method of claim 1, wherein collecting the sweat sample includes collecting sweat from one of the following: a gland directly caused to sweat by the sweat stimulant, or a gland indirectly caused to sweat by the sweat stimulant.

9. The method of claim 1, wherein the duration is greater than or equal to 12 hours.

10. The method of claim 1, wherein the minimum sweat generation rate is greater than 5 nL/min/gland.

11. The method of claim 1, wherein the applying includes applying a charge density that is equal to or less than 1 mC/cm$^2$/day.

12. The method of claim 1, wherein the applying includes applying a charge that is less than 1 mC/day.

13. The method of claim 1, wherein an amount of sweat generated per gland is greater than 350 nL/gland/dose.

14. The method of claim 1, wherein the duration is greater than 30 hours.

15. The method of claim 1, wherein the duration is greater than 24 hours.

16. The method of claim 1, wherein the sweat stimulant is effective to generate sweat for an average sweat stimulant duration, and wherein the plurality of doses is greater than or equal to a quotient between the duration divided by the average sweat stimulant duration.

17. The method of claim 16, wherein applying the plurality of doses comprises:

applying the first dose at the beginning of the duration; and applying each of the at least one subsequent dose at or before the end of the average sweat stimulant duration of each previous dose.

18. The method of claim 1, wherein the applying comprises applying a charge density equal to or less than 160 mC/cm$^2$/day.

19. The method of claim 1, wherein the applying comprises applying a charge density equal to or less than 80 mC/cm$^2$/day.

20. The method of claim 1, wherein the applying comprises applying a charge density equal to or less than 40 mC/cm$^2$/day.

21. The method of claim 1, wherein the charge density is applied to a single area of skin that is less than or equal to 0.5 cm$^2$.

22. The method of claim 1, wherein the predetermined sweat rate is 1 nL/min/gland.

23. A method comprising:

applying a plurality of doses of a sweat stimulant to skin effective to generate sweat at or above a minimum sweat generation rate for a duration, wherein the applying comprises applying a charge density that is equal to or less than 10 mC/cm$^2$/day, wherein the minimum sweat generation rate is greater than or equal to 0.1 nL/min/gland, wherein the sweat stimulant is selected from the group consisting of acetylcholine, carbachol, methacholine, bethanechol, muscarine, pilocarpine, oxotremorine, or a combination thereof, and wherein the duration is greater than or equal to six hours;

collecting a sweat sample from the skin;

measuring a sweat generation rate to establish a measured sweat generation rate for the duration;

wherein applying the plurality of doses comprises:

applying a first dose; and applying at least one subsequent dose in response to the measured sweat generation rate falling below a predetermined sweat rate during the duration, the predetermined sweat rate being greater than the minimum sweat generation rate; and receiving a measurement of a characteristic of an analyte in the sweat sample.

24. The method of claim 23, wherein the applying comprises applying a charge density equal to or less than 5 mC/cm$^2$/day.

25. The method of claim 23, wherein the sweat stimulant is effective to generate sweat for an average sweat stimulant duration, and wherein the plurality of doses is greater than or equal to a quotient between the duration divided by the average sweat stimulant duration.

26. The method of claim 25, wherein applying the plurality of doses comprises:

applying the first dose at the beginning of the duration; and applying each of the at least one subsequent dose at or before the end of the average sweat stimulant duration of each previous dose.

27. The method of claim 23, wherein the predetermined sweat rate is 1 nL/min/gland.

* * * * *